US009409153B2

(12) United States Patent
Yang et al.

(10) Patent No.: US 9,409,153 B2
(45) Date of Patent: Aug. 9, 2016

(54) SUPPORTED MO—O—K—ME$_x$O$_y$ CATALYST FOR THE SYNTHESIS OF METHANETHIOL FROM HIGH H$_2$S-CONTAINING SYNGAS

(75) Inventors: Yiquan Yang, Xiamen (CN); Yingjuan Hao, Xiamen (CN); Aiping Chen, Xiamen (CN); Qi Wang, Xiamen (CN); Lingmei Yang, Xiamen (CN); Qiaoling Li, Xiamen (CN); Shenjun Dai, Xiamen (CN); Weiping Fang, Xiamen (CN); Jan-Olaf Barth, Frankfurt (DE); Christoph Weckbecker, Gruendau-Lieblos (DE); Klaus Huthmacher, Gelnhausen (DE)

(73) Assignee: EVONIK DEGUSSA GMBH, Essen (DE)

( * ) Notice: Subject to any disclaimer, the term of this patent is extended or adjusted under 35 U.S.C. 154(b) by 584 days.

(21) Appl. No.: 12/810,688

(22) PCT Filed: Nov. 28, 2008

(86) PCT No.: PCT/EP2008/066451
§ 371 (c)(1),
(2), (4) Date: Jun. 25, 2010

(87) PCT Pub. No.: WO2009/083368
PCT Pub. Date: Jul. 9, 2009

(65) Prior Publication Data
US 2010/0286448 A1 Nov. 11, 2010

(30) Foreign Application Priority Data
Dec. 28, 2007 (CN) .......................... 2007 1 0305947

(51) Int. Cl.
| B01J 21/08 | (2006.01) |
| B01J 23/04 | (2006.01) |
| B01J 23/28 | (2006.01) |
| B01J 23/88 | (2006.01) |
| B01J 23/882 | (2006.01) |
| B01J 23/883 | (2006.01) |
| B01J 23/00 | (2006.01) |
| B01J 23/887 | (2006.01) |
| B01J 37/02 | (2006.01) |
| B01J 37/16 | (2006.01) |
| C07C 319/02 | (2006.01) |
| B01J 21/06 | (2006.01) |

(52) U.S. Cl.
CPC ............... *B01J 23/28* (2013.01); *B01J 23/002* (2013.01); *B01J 23/8872* (2013.01); *B01J 37/0207* (2013.01); *B01J 37/16* (2013.01); *C07C 319/02* (2013.01); *B01J 21/063* (2013.01); *B01J 2523/00* (2013.01)

(58) Field of Classification Search
CPC ......... C07C 319/06; B01J 21/06; B01J 23/28; B01J 21/08; B01J 23/8872; B01J 37/027; B01J 37/16; B01J 2523/13; B01J 2523/68; C23C 18/16; C23C 18/54
USPC ........... 502/73, 211, 243, 302, 303, 304, 309, 502/313, 315, 316, 317
See application file for complete search history.

(56) References Cited

U.S. PATENT DOCUMENTS

| 7,247,376 B1 * | 7/2007 | Chen et al. .................... 428/403 |
| 2007/0213564 A1 | 9/2007 | Yang et al. |

FOREIGN PATENT DOCUMENTS

| CN | 1207957 | 2/1999 |
| CN | 1207958 | 2/1999 |
| CN | 1528515 | 9/2004 |
| CN | 1528516 | 9/2004 |
| CN | 1559676 A | 1/2005 |
| EP | 0 167 354 | 1/1986 |
| JP | 2007-508256 | 4/2007 |
| JP | 2007-119900 | 5/2007 |
| WO | 2005/040082 | 5/2005 |

OTHER PUBLICATIONS

International Search Report for PCT/EP2008/066451 mailed Nov. 23, 2009.
Chen et al., "Direct synthesis of methanethiol from H$_2$S-rich syngas over sulfided Mo-based catalysts", Journal of Molecular Catalysis A, Chemical, vol. 283, No. 1-2, 2007, pp. 69-76.
Chen et al., "Catalytic Synthesis of Methanethiol from H$_2$S-rich Syngas Over Sulfided SiO$_2$-suported Mo-based Catalysts", Catalysts Letters, vol. 12, No. 3-4, 2007, pp. 260-265.
Henry et al., "Electroless (Autocatalytic) Plating", Metal Finishing, vol. 105, No. 10, 2007, pp. 350-356.
Liu et al., "The effect of acetic acid pretreatment for cobalt catalysts prepared from cobalt nitrate", Catalysis Communications, vol. 8, No. 5, 2007, pp. 773-776.

(Continued)

*Primary Examiner* — Jun Li
(74) *Attorney, Agent, or Firm* — Smith, Gambrell & Russell, LLP

(57) ABSTRACT

This invention is related to a preparation method of a supported catalyst Mo—O—K-Me$_x$O$_y$ for the synthesis of methanethiol from H$_2$S-containing syngas. The catalyst comprises of an active component of Mo—O—K-based species, an active promoter and a support denoted as metal (or metals)-carrier. The support is prepared by electroless plating method in such a way that the metal or metals chosen are plated onto the surface of the carrier. Transition metal, especially Fe, Co or Ni are selected to be the plating metal, while SiO$_2$, Al$_2$O$_3$ or TiO$_2$ are selected to be carrier. The catalyst thus prepared is found to be efficient for the synthesis of methanethiol from H$_2$S-containing syngasor carbon oxides/hydrogen mixtures, especially regarding a minor formation of the by-product CO$_2$.

12 Claims, No Drawings

(56) References Cited

OTHER PUBLICATIONS

PCT Notification Concerning Transmittal of International Preliminary Report on Patentability (Form PCT/IB/326) for PCT/EP2008/066451 mailed Jul. 8, 2010 (in English language).

PCT International Preliminary Report on Patentability (Form PCT/IB/373) for PCT/EP2008/066451 dated Jun. 10, 2010 (in English language).

PCT Written Opinion of the International Searching Authority (Form/ISA/237) for PCT/EP2008/066451 dated Jun. 10, 2010 (in English language).

Notification of Reason for Refusal dated Oct. 12, 2012 for Japanese Application No. 2010-540091 (in English).

Chinese Office Action issued Mar. 5, 2013 for Application No. 200710305947.3 (English language translation attached).

* cited by examiner

SUPPORTED MO—O—K—ME$_x$O$_y$ CATALYST FOR THE SYNTHESIS OF METHANETHIOL FROM HIGH H$_2$S-CONTAINING SYNGAS

The present invention relates to a preparation method of a supported Mo—O—K-Me$_x$O$_y$ catalyst for the synthesis of methanethiol from high H$_2$S-containing syngas, therein support is a metal (or metals)-plated carrier, especially metal (or metals)-plated-SiO$_2$, which is made by electroless plating method.

THE PRIOR ART

As an important chemical material used to produce methionine, pesticides and medicine, methanethiol is predominantly prepared by the reaction of hydrogen sulfide with methanol. The direct synthesis of methanethiol from the reaction of H$_2$S with carbon oxides, in particular, from H$_2$S-containing syngas is an attractive alternative. For example, EP167,354 disclosed a synthesis pathway from the reaction of hydrogen sulfide with carbon monoxide in the presence of a catalyst NiO or MoO$_3$ supported on TiO$_2$; Chinese patent CN98118186.4 and CN98118187.2 disclosed Mo—S—K/SiO$_2$ catalysts used for methanethiol synthesis from high H$_2$S-containing syngas; Chinese patent appl.200310100496.1 and 200310100495 reported Mo—O—K/SiO$_2$ catalysts promoted by transition metal oxides or rare earth metal oxides for the methanethiol synthesis, herein the promoters were selected from the oxides of Co, Ni, Fe, Mn or the rare earth oxides of La, Ce, the active component Mo—O—K base are formed from the precursor K$_2$MoO$_4$ or (NH$_4$)$_6$Mo$_7$O$_{24}$.4H$_2$O plus potassium salt. Those catalysts were prepared by traditional impregnation method. The catalysts exhibit high selectivity and space-time-yield of methyl mercaptan, but produce also by-products, such as carbonyl sulfide, methane and dimethyl sulfide.

STATEMENT OF THE INVENTION

The object of this invention is to develop a further improved solid supported Mo—O—K-Me$_x$O$_y$ catalyst with high activity and selectivity of methanethiol, but lower selectivity of CO$_2$.

DETAILED DESCRIPTION OF THE INVENTION

The object of the invention is a catalyst comprising:
a) a support, consisting of a porous carrier and a metal A deposited thereon by electroless deposition of metal on the carrier;
b) a Mo—O—K based active component; and
c) optionally an active promoter Me$_x$O$_y$, chosen from the group of transition metal oxides or rare earth metal oxides or rare earth metal oxides, wherein x and y depend on the valence of the metal.

The catalyst comprises an active component, optionally an active promoter and a support. Said active component is a Mo—O—K-based component. Said promoter is at least one chosen from the group of transition metal oxides, or rare earth metal oxides, comprising especially from the oxides of iron, cobalt, Nickel, manganese, lanthanum and cerium, and expressed as Me$_x$O$_y$, wherein "Me" denotes the metal selected from the group of transition metals of rare earth metals, especially Fe, Co, Ni, Mn, La or Ce.

Said support is a metal (or metals)-plated carrier, especially metal (or metals)-SiO$_2$, which is made by electroless plating method. In general the carrier used is porous and chosen from the group of SiO$_2$, Al$_2$O$_3$, TiO$_2$, Zeolites, especially SiO$_2$. Said metal or metals plated on said carrier can be selected from the group of Ni, Co or Fe, preferably Ni or Co.

When potassium molybdate is used as precursor of the Mo—O—K-based component, the catalyst of present invention is denoted as K$_2$MoO$_4$-Me$_x$O$_y$/Metal-carrier, wherein the weight ratios of the components of the catalyst are K$_2$MoO$_4$/Me$_x$O$_y$/metal-carrier=(1-30)/(0.0-25.0)/(0.1-10.0)-100, preferably (15-20)/(0.0-25.0)/(0.5-8.0)-100;

when (NH$_4$)$_6$Mo$_2$O$_{24}$.4H$_2$O plus one of potassium salts or MoO$_3$ plus one of potassium salts serve as precursors of the Mo—O—K-based compound, the catalyst of the present invention is expressed as MoO$_3$—K$_2$O-Me$_x$O$_y$/metal-carrier, wherein the weight ratios of the components of the catalyst are:

MoO$_3$/K$_2$O/Me$_x$O$_y$/metal-carrier=(1-30)/(1-20)/(0.0-25.0)/(0.1-10.0)-100, preferably (15-20)/(10-15)/(0.0-25.0)/(0.5-8.0)-100; Said potassium compound is at least one chosen from the group, comprising K$_2$CO$_3$, KOH, KNO$_3$ and CH$_3$COOK.

Chemically metal-plating method is used to prepare said metal (or metals)-carrier the metal (or metals) chosen is plated onto the carrier chosen, wherein the weight ratio of metal (or metals)/carrier is (0.1-10.0)/100, preferably (0.5-8.0)/100.

The invention is also directed to the preparation of said catalysts by multi-step impregnation.

In order to distribute the active component more equally over the support, at least one chelating reagent should be used in the impregnation process.

Said chelating or coordinating reagent is at least one chosen from the group comprising citric acid, ammonium citrate, L-glutamic acid, tartaric acid and ethylenediaminetetraacetic acid(EDTA); the amount of chelating agent added correspondingly is 0.1-0.6 times as much by weight as that of the support, more preferably is 0.3-0.6 times as much as that of the support. Suitable amounts of ammonia are added to adjust the pH value of the steeping liquor to 7.0-13.0, preferable 8.0-12.0.

The activation of the carrier by chemically plating metal proceeds as follows (shown as a preferred method):
(1) the preparation of metal-plating solution:

A given quantity of soluble metal salt chosen and a given quantity of coordinating agent are dissolved in a given quantity of distilled water successively to produce a metal-plating solution, in which the concentration of the metal ions varies from 1 g/l to 20 g/l, preferably 5-7 g/l; the coordinating agent is at least one chosen from Na$_3$C$_6$H$_5$O$_7$.2H$_2$O, C$_6$H$_8$O$_7$.H$_2$O, C$_2$H$_8$N$_2$ or NaKC$_4$H$_4$O$_6$.4H$_2$O, the concentration of the coordinating agent varies from 1 g/l to 20 g/l.

Keeping stirring for 10 minutes, then a given quantity of the stabilizing agents (NH$_4$)$_2$SO$_4$ or Na$_3$C$_6$H$_5$O$_7$.2H$_2$O, is added subsequently to the plating solution obtained above followed by stirring for another 20 minutes, followed by adding some NH$_3$.H$_2$O to adjust the pH of the plating solution to 7.0-13.0, preferably 8.0-12.0; finally, a suitable amount of distilled water is added to adjust the volume of the solution in such a way that the concentration of metal salt chosen in the plating solution varies from 1 g/l to 20 g/l, preferably 5-7 g/l.

(2) Pretreatment of the carrier:
  Prior to plating the metal onto the carrier, the carrier is preferably pretreated by the following processes:
  a) the carrier should be washed with distilled water, and then dried, followed by immersing the clean carrier in a solution of 4.5 mol/l $H_2SO_4$+0.88 mol/l $H_2O_2$ (1:1) for 5 minutes under agitating, and subsequently washed with distilled water three times;
  b) the cleaned carrier is immersed in an aqueous solution of activation agent under agitation, said activation agent is preferably $PdCl_2$/HCl, the concentration of the activation agent varies in general from 0.05 g/l to 1.0 g/l, preferably from 0.1 g/l to 0.5 g/l; keeping ultrasonically agitating for e.g. 30-35 minutes, then washing with distilled water three times;
  c) the activated carrier is immersed in an aqueous solution of a reducing agent under agitation; the reducing agent is preferably $NaH_2PO_4$ or $NaBH_4$; the concentration of the agent varies from 20 g/l to 30 g/l;
(3) Plating of metal onto carrier is conducted by putting the pretreated carrier produced in step (2) into the plating solution of the metal chosen at 40-85° C. for 30-40 minutes. The metal-platted carrier is washed with distilled water e.g. for three times and then dried at about 110° C. for about 6 hours. The metal-plated carrier is termed support, such as support Ni—$SiO_2$ or Co—$SiO_2$.

Impregnation of the Support with the Active Component (Shown as a Preferred Method)

(1) A given quantity of said precursor $K_2MoO_4$ or $(NH_4)_6Mo_7O_{24}$ plus a potassium salt or $MoO_3$ plus a soluble potassium compound and suitable amount of chelating agent are dissolved in distilled water to generate an impregnation solution; into which then a suitable amount of $NH_3.H_2O$ is dropped to adjust the pH of the impregnation solution at 8-12, preferably 8-10; then the metal-plated carrier (30-45 meshes) produced in step (3) of carrier activation is soaked in the impregnation solution at room temperature for 12 hours, then dried at 120° C. for 5 hours to produce the desired supported Mo—O—K catalyst.

(2) Alternatively, a given quantity of said precursor $K_2MoO_4$ or $(NH_4)_6Mo_7O_{24}$ plus a soluble potassium compound or $MoO_3$ plus a potassium salt are dissolved in distilled water, then a suitable amount of $NH_3.H_2O$ is dropped into the solution to make the precursor fully dissolved in the distilled water to generate an impregnation solution, which contains only an active component.

In a preferred case a given quantity of soluble transition metal salt or rare earth metal salt chosen, especially, its sulfate, nitrate or acetate, and suitable amount of chelating agent are added to the above described solution, into which a suitable amount of $NH_3.H_2O$ is then dropped to adjust the pH of the impregnation solution at 8-12, preferably 8-10; lastly the metal (or metals)-plated carrier (30-45 meshes) produced in step (3) of carrier activation is soaked in the impregnation solution at room temperature for 12 hours, then filtered and dried at 110° C. for 6 hours to produce the desired supported Mo—O—K—$Me_xO_y$ catalyst.

Said catalyst is used for a method to prepare methanethiol from high $H_2S$-containing syngas. The reaction conditions are known from the state of art.

The catalyst should be sulfided for 8-10 h before using.

The reactivity evaluation of the catalyst of present invention was carried out in a fixed-bed tubular reactor with 0.5 ml of catalyst per pass. The reaction conditions are preferably CO/$H_2$/$H_2S$=1/1/2, 250-350° C., about 0.05-0.3 MPa and GHSV=500-3000 $h^{-1}$. The products were analyzed by GC. All date were taken after the steady state achieved.

The assay results show that the catalyst of the present invention were not only has high catalytic activity for the synthesis of methanethiol from high $H_2S$-containing syngas, but also has high selectivity of methanethiol, but less selectivity of $CO_2$.

The following examples illustrate the present invention further.

Example 1

Electroless Plating (1) 2.0 g of $NiSO_4.7H_2O$ and 2.0 g of $Na_3C_6H_5O_7.2H_2O$ were dissolved in 50 ml of distilled water successively to produce a plating solution, keeping stirring for 10 minutes, then 3.0 g of $(NH_4)_2SO_4$ and 3.0 g of $NaH_2PO_4.H_2O$ were added one after another to the solution obtained above, stirring for another 20 minutes, followed by adding some $NH_3.H_2O$ to adjust the pH of the solution to 9.0; finally, distilled water was added to adjust the volume of the solution to 100 ml in such a way that the concentration of $NiSO_4$ in the plating solution is 20 g/l;

(2) 10 g of clean $SiO_2$ was immersed in 20 ml of 4.5 mol/l $H_2SO_4$+0.88 mol/l $H_2O_2$(1:1) solution for 5 minutes under agitating, and then washed for three times with distilled water; followed by immersing the carrier $SiO_2$ in 20 ml of 0.1 g/l $PdCl_2$/HCl solution, keeping ultrasonically agitating for 30 minutes, and then washed for three times with distilled water; the next step was to immerse the activated carrier $SiO_2$ in 10 ml of 30 g/l $NaH_2PO_4$ solution, at the same time agitating for 10 seconds and repeated the reduced experiment step again, so as to form an activated carrier.

(3) The electroless plating process was carried out by immersing the activated carrier $SiO_2$ in the plating solution prepared in step (2) at appr. 40° C. for 30 minutes. After plating, the Ni-plated $SiO_2$ was washed with distilled water three times and dried at 383K for 4 h. The weight ratio of metal over carrier of the support thus prepared was Ni—$SiO_2$=4.4-100.

(4) 0.45 g of $K_2MoO_4$ and 3.0 g of tartaric acid were dissolved in 6 ml of distilled water to generate an impregnation solution, into which then 0.8 ml of $NH_3.H_2O$ was dropped to adjust the pH of the impregnation solution at 9. Then 3 g of support Ni—$SiO_2$ (30-45 meshes) produced in step (3) was soaked in the impregnation solution at room temperature for 12 hours, then dried at 110° C. for 5 hours. The weight ratio of every component of the catalyst was $K_2MoO_4$/Ni—$SiO_2$=15/(4.4-100). The evaluation result of the catalyst thus prepared is shown in table 1.

Example 2, 3, 4

The catalysts were prepared according to the experiment steps described in Example 1, but the concentration of the plating solution was respectively diluted by once, twice three times with distilled water, namely the nickel ion concentration was respectively 10 g/1, 6.67 g/1, 5 g/l. The weight ratio of every content of the catalysts gained was $K_2MoO_4$/Ni—$SiO_2$=15/(2.2-100), $K_2MoO_4$/Ni—$SiO_2$=15/(1.5-100), $K_2MoO_4$/Ni—$SiO_2$=15/(1.1-100) respectively. The evaluation results of the catalysts thus prepared were also shown in table 1.

Example 5, 6

The catalysts were prepared according to the experiment steps described in Example 1, but the weight of carrier $SiO_2$ to be plated was respectively 8 g and 6 g. The weight ratio of every content of the catalysts gained was $K_2MoO_4/Ni-SiO_2=15/(5.5-100)$ and $K_2MoO_4/Ni-SiO_2=15/(7.3-100)$, respectively. The evaluation results of the catalysts thus prepared are also shown in table 1.

TABLE 1 performance of the catalysts $K_2MoO_4/Ni-SiO_2$ in examples 1-6

| examples | $K_2MoO_4/$ Ni—SiO$_2$ | selectivity | | | | $CO_2/$ CH$_3$SH | CO % conversion |
|---|---|---|---|---|---|---|---|
| | | CH$_4$ | CH$_3$SH | COS | CO$_2$ | | |
| 1 | 15/(4.4-100) | 0.0226 | 46.84 | 18.91 | 34.02 | 0.7265 | 56.84 |
| 2 | 15/(2.2-100) | 0.0216 | 46.31 | 20.33 | 33.14 | 0.7156 | 63.45 |
| 3 | 15/(1.5-100) | 0.0202 | 46.61 | 20.67 | 32.70 | 0.7017 | 65.61 |
| 4 | 15/(1.1-100) | 0.0130 | 43.37 | 24.91 | 31.70 | 0.7311 | 49.16 |
| 5 | 15/(5.5-100) | 0.0207 | 46.70 | 19.01 | 34.27 | 0.7338 | 56.57 |
| 6 | 15/(7.3-100) | 0.0196 | 46.85 | 19.14 | 34.99 | 0.7255 | 55.46 |

Example 7, 8, 9, 10, 11

The catalysts were prepared according to the experiment steps described in Example 3, but the weight ratio of $K_2MoO_4$/support varied from 5/100, 10/100, 15/100, 20/100, 25/100. The weight ratio of every component of the catalysts gained was $K_2MoO_4/Ni-SiO_2=5/(1.5-100)$, $K_2MoO_4/Ni-SiO_2=10/(1.5-100)$, $K_2MoO_4/Ni-SiO_2=15/(1.5-100)$, $K_2MoO_4/Ni-SiO_2=20/(1.5-100)$, $K_2MoO_4/Ni-SiO_2=25/(1.5-100)$ respectively. The evaluation results of the catalysts thus prepared were also shown in table 2.

Example 12

(1) 0.667.0 g of $NiSO_4.7H_2O$ and 0.667 g of $Na_3C_6H_5O_7.2H_2O$ were dissolved into 50 ml of distilled water successively to produce a plating solution, keeping stirring for 10 minutes, then 1.0 g of $(NH_4)_2SO_4$ and 1.0 g of $NaH_2PO_4.H_2O$ were added one after another to the solution obtained above, stirring for another 20 minutes, followed by adding some $NH_3.H_2O$ to adjust the pH of the solution to 9.0; finally, distilled water was added to adjust the volume of the solution to 100 ml in such a way that the concentration of $NiSO_4$ in the plating solution was 4.12 g/l;

(2) 10 g of clean $SiO_2$ were immersed in 20 ml of 4.5 mol/l $H_2SO_4+0.88$ mol/l $H_2O_2$(1:1) solution for 5 minutes under agitation, and then washed for three times with distilled water, followed by immersing the carrier $SiO_2$ in 20 ml of 0.1 g/l $PdCl_2/HCl$ solution, at the same time keeping ultrasonically agitating for 30 minutes, and then washed for three times with distilled water; the next step was to immerse the activated carrier $SiO_2$ in 10 ml of 30 g/l $NaH_2PO_4$ solution, at the same time agitating for 10 seconds; finely repeated the reduced experiment step again to produce an activated carrier $SiO_2$.

(3) The electroless plating process was carried out by immersing the activated carrier $SiO_2$ in the plating solution prepared in step (2) at 42° C. for 30 minutes. After plating, the Ni-plated $SiO_2$ was washed with distilled water four times and then dried at 110° C. for 6 hours. The weight ratio of the two contents of the support thus prepared was $Ni-SiO_2=1.5-100$.

(4) 0.496 g of $K_2MoO_4$ and 1.0 ml of $NH_3.H_2O$ were dissolved in 5 ml of distilled water to generate an impregnation solution; then 0.5 g of tartaric acid and 0.135 g of $Ni(NO_3)_2.6H_2O$ were added to the $K_2MoO_4$ solution, the pH value of the $K_2MoO_4$ solution was measured to be at 9; then 3 g of support nickel-plated $SiO_2$ (30-45 meshes) produced in step (3) was soaked in the impregnation solution at room temperature for 12 hours, then dried at 110° C. for 6 hours. The weight ratio of every component of the catalyst thus prepared was $K_2MoO_4/NiO/Ni-SiO_2=15/1.0/(1.5-100)$. The evaluation result of the catalyst thus prepared is shown in table 3.

Example 13

The catalyst was prepared according to the experiment steps described in Example 12, but 0.1346 g of $Co(NO_3)_2.6H_2O$ substituted for 0.135 of $Ni(NO_3)_2.6H_2O$. The weight ratio of every component of the catalyst thus prepared was $K_2MoO_4/CoO/Ni-SiO_2=15/1.0/(1.5-100)$. The evaluation result of the catalyst thus prepared is also shown in table 3

Example 14

The catalyst was prepared according to the experiment steps described in Example 1, but $NiSO_4.7H_2O$ for preparing plating solution was replaced by $CoSO_4.7H_2O$, the amount of $CoSO_4.7H_2O$ is the same as that of $NiSO_4.7H_2O$, but the Ph value of the plating solution was adjusted by $NH_3.H_2O$ to 12; the plating process of the activated carrier $SiO_2$ was carried out at 80° C. The weight ratio of every component of the catalyst gained was $K_2MoO_4/(Co-SiO_2)=15/(4-100)$. The evaluation result of the catalyst thus prepared was shown in table 4

Example 15

The catalyst was prepared according to the experiment steps described in Example 12, but 0.667 g of $NiSO_4.7H_2O$ for preparing plating solution was replaced by 0.667 g of $CoSO_4.7H_2O$; while the quantity of $Ni(NO_3)_2.6H_2O$ for preparing promoter $Me_xO_y$ was 0.117 g. The weight ratio of every component of the catalyst gained was $K_2MoO_4/NiO/Co-SiO_2=15/1/(1.5-100)$. The evaluation result of the catalyst thus prepared is also shown in table 4

Example 16

The catalyst was prepared according to the experiment steps described in Example 15, but 0.117 g of $Ni(NO_3)_2.6H_2O$ for preparing promoter $Me_xO_y$ was replaced by 0.117 g of $Co(NO_3)_2.6H_2O$. The weight ratio of every component of the catalyst gained was $K_2MoO_4/CoO/Co-SiO_2=15/1/(1.5-100)$. The evaluation result of the catalyst thus prepared is also shown in table 4

Example 17

The catalyst was prepared according to the experiment steps described in Example 1, but 0.45 g $K_2MoO_4$ and 0.5 g tartaric acid were replaced by 3.00 g of $(NH_4)_6Mo_7O_{24}.4H_2O$ plus 0.45 g of $KNO_3$ and 0.5 g of citric acid respectively. The weight ratio of every component of the catalyst gained was $MoO_3/K_2O/(Ni-SiO_2)=11/4/(4-100)$. The evaluation result of the catalyst thus prepared is shown in table 5

Example 18

The catalyst was prepared according to the experimental steps described in Example 12, but 0.496 g $K_2MoO_4$ was replaced by 3.00 g of $(NH_4)_6Mo_7O_{24}.4H_2O$ plus 0.22 g of $K_2CO_3$. The weight ratio of every component of the catalyst gained was $MoO_3/K_2O/NiO/(Ni-SiO_2)=11/4/0.25/(1.5-100)$. The assay result of the catalyst thus prepared was shown in table 5.

TABLE 2 performance of catalysts $K_2MoO_4/Ni-SiO_2$ in examples 7-11

| examples | $K_2MoO_4/$ $(Ni-SiO_2)$ | Selectivity, % | | | | $CO_2/$ $CH_3SH$ | CO Conversion, % |
|---|---|---|---|---|---|---|---|
| | | $CH_4$ | $CH_3SH$ | COS | $CO_2$ | | |
| 7 | 5/(1.5-100) | 0.0956 | 28.74 | 40.12 | 31.04 | 1.080 | 30.21 |
| 8 | 10/(1.5-100) | 0.0353 | 38.13 | 28.64 | 33.20 | 0.871 | 43.15 |
| 9 | 15/(1.5-100) | 0.0282 | 46.61 | 16.79 | 36.57 | 0.785 | 65.61 |
| 10 | 20/(1.5-100) | 0.0339 | 35.96 | 33.47 | 30.23 | 0.841 | 58.96 |
| 11 | 25/(1.5-100) | 0.0496 | 30.38 | 38.24 | 31.33 | 1.030 | 59.63 |

TABLE 3 performance of catalysts $K_2MoO_4-NiO/Ni-SiO_2$ in examples 10-11

| examples | catalysts | Selectivity, % | | | | $CO_2/CH_3SH$ | CO % conversion |
|---|---|---|---|---|---|---|---|
| | | $CH_4$ | $CH_3SH$ | COS | $CO_2$ | | |
| 12 | $K_2MoO_4/NiO/(Ni-SiO_2) =$ 25/1.7/(1.5-100) | 0.0257 | 37.63 | 19.94 | 42.40 | 1.127 | 69.26 |
| 13 | $K_2MoO_4/CoO/(Ni-SiO_2) =$ 25/2.6/(1.5-100) | 0.0214 | 37.64 | 19.10 | 43.24 | 1.148 | 62.58 |

TABLE 4 performance of catalysts $K_2MoO_4/Co-SiO_2$ in examples 14-16

| examples | catalysts | Selectivity, % | | | | $CO_2/CH_3SH$ | CO % conversion |
|---|---|---|---|---|---|---|---|
| | | $CH_4$ | $CH_3SH$ | COS | $CO_2$ | | |
| 14 | $K_2MoO_4/(Co-SiO_2) =$ (15/4.4-100) | 0.01675 | 42.42 | 17.05 | 40.51 | 0.9550 | 36.33 |
| 15 | $K_2MoO_4/NiO/(Co-SiO_2) =$ 15/1.0/(1.5-100) | 0.01507 | 46.15 | 23.66 | 30.17 | 0.6538 | 24.77 |
| 16 | $K_2MoO_4/CoO/(Co-SiO_2) =$ 15/1/(1.5-100) | 0.01459 | 35.74 | 16.91 | 34.33 | 0.7705 | 24.64 |

TABLE 5 performance of catalysts $K_2MoO_4-NiO/Ni-SiO_2$ in examples 17-18

| examples | catalysts | Selectivity, % | | | | $CO_2/CH_3SH$ | CO % conversion |
|---|---|---|---|---|---|---|---|
| | | $CH_4$ | $CH_3SH$ | COS | $CO_2$ | | |
| 17 | $MoO_3/K_2O/(Ni-SiO_2) =$ 11/4/(4.4-100) | 0.0226 | 45.57 | 19.91 | 34.22 | 0.7466 | 56.84 |
| 18 | $MoO_3/K_2O/NiO/Ni-SiO_2 =$ 11/4/0.25/(1.5-100) | 0.0283 | 39.55 | 22.21 | 38.20 | 0.9658 | 60.32 |

The invention claimed is:

1. A catalyst comprising
    a) a support consisting of a porous carrier and a metal A selected from Ni or Co, wherein the porous carrier is $SiO_2$ and the metal A is deposited on the carrier by electroless deposition to form an activated metal carrier;
    b) a Mo—O—K based active component impregnated on the activated metal carrier, wherein the Mo—O—K based active component is $K_2MoO_4$ or $MoO_3$ and $K_2O$; and
    c) optionally an active promoter $Me_xO_y$, which is impregnated on the activated metal carrier, where Me is Ni or Co, wherein x and y depend on the valence of the metal, and
    wherein the weight ratios of the catalyst are:

$K_2MoO_4/Me_xO_y/metalA$-carrier$=(5-20)/(0.0-25.0)/$
    $(0.5-8.0)$-100; or $MoO_3/K_2O/Me_xO_y/metalA$-carrier$=(15-20)/(10-15)/$
    $(0.0-25.0)/(0.5-8.0)$-100.

2. The catalyst according to claim 1, wherein the support comprises reduced Pd and P components.

3. Method of producing the catalyst of claim 1 comprises the steps:
    a) activating a $SiO_2$ carrier, wherein the activation comprises the steps of first treating the carrier with a solution of a Pd-component and a reducing agent;
    b) impregnating said treated carrier with a solution comprising a solution of a metal salt whereby the metal is chosen from the group comprising Co and Ni, to achieve electroless deposition of said metal on the treated carrier to produce the catalyst support;

c) impregnating said support with an impregnation liquid of an aqueous solution of $K_2MoO_4$ or $(NH_4)Mo_7O_{24}$ plus a potassium compound or $MoO_3$ plus a potassium compound; and optionally a precursor of said active promoter $Me_xO_y$, wherein Me is Ni or Co, followed by drying the received product to obtain the desired catalyst.

4. The process according to claim 3, wherein said support is prepared by electroless plating method, the preparation processes include:

(i) the preparation of metal-plating solution;

a given quantity of soluble metal salt wherein the metal salt is chosen from Ni or Co salt, chosen and a given quantity of coordinating agent are dissolved in given quantity of distilled water successively to produce a metal-plating solution, in which the concentration of the metal ion varies from 1 g/l to 20 g/l, preferably 5-7 g/l; keeping stirring for 10 minutes, then a given quantity of a stabilizing agent are added one after another to the plating solution obtained above, stirring for another 20 minutes, followed by adding some $NH_3.H_2O$ to adjust the pH of the plating solution to 7.0-13.0, preferably 8.0-12.0; finally, suitable amount of distilled water is used to adjust the volume of the solution in such a way that the concentration of metal salt chosen in the plating solution varies from 1 g/l to 20 g/l, preferably 5-7 g/l;

(ii) pretreatment of the $SiO_2$ carrier chosen comprising the steps of a) the carrier should be washed with distilled water, and then dried, followed by treatment of the clean carrier by immersing it into a solution of 4.5 mol/$1H_2SO_4$+0.88 mol/$1H_2O_2$ (1:1) for 5 minutes under agitating, and then washed with distilled water three times;

b) the cleaned carrier is immersed in an aqueous solution of activation agent under agitation, said activation agent is $PdCl_2$/HCl, the concentration of the activation agent varies from 0.05 g/l to 1.0 g/l, preferably from 0.1 g/l to 0.5 g/l; keeping ultrasonically agitating for 30-35 minutes, then washed with distilled water three times;

c) the activated carrier is immersed in an aqueous solution of reduction agent under agitation, the concentration of the reduction agent varies from 20 g/l to 30 g/l, keeping agitating for 10 seconds;

(iii) plating of metal onto carrier is conducted by putting the activated carrier produced in step (2) into the plating solution at 30-90° C. for 30-40 minutes, wherein the metal-platted carrier is washed with distilled water three times and then dried at 110° C. for 6 hours.

5. The process according to claim 3, wherein said reduction agent is $NaH_2PO_3.H_2O$ or $NaBH_4$.

6. The process according to claim 3, wherein said stabilizing agent is ammonium sulfate or ammonium chloride.

7. The process according to claim 3, wherein said coordinating agent is at least one chosen from $Na_3C_6H_5O_7.2H_2O$, $C_6H_8O_7.H_2O$, $C_2H_8N_2$ or $NaKC_4H_4O_6.4H_2O$, the concentration of the chelating agent varies from 1 g/l to 60 g/l.

8. The process according to claim 3, wherein the pH value of the electroless plating solution varies from 7.0 to 13.0, preferably from 8.0 to 12.0.

9. The process according to claim 4, wherein at least one chelating reagent should present in the imprecation solution.

10. The process according to claim 4, wherein the chelating reagent is chosen from the group of citric acid, ammonium citrate tribasic, L-glutamic acid, tartaric acid and ethylenediaminetetraacetic acid(EDTA); and the amount of chelating agent added correspondingly is 0.1-0.6 times as much as that of the support, more preferably is 0.3-0.6 times as much as that of the support.

11. The process according to claim 3, wherein the pH value of the impregnation solution is adjusted to 8-12, preferably 8-10 by ammonia.

12. A method for preparing methyl mercaptan in a catalytic process comprising:

a) providing the supported catalyst of claim 1; and b) utilizing said catalyst reacting carbon oxides, sulphur and/or hydrogen sulphide and hydrogen to form methyl mercaptan.

* * * * *